United States Patent [19]
Tamura

[11] Patent Number: 6,095,685
[45] Date of Patent: *Aug. 1, 2000

[54] X-RAY RADIOSCOPIC APPARATUS

[75] Inventor: Joichi Tamura, Ibaraki-ken, Japan

[73] Assignee: Hitachi Medical Corporation, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/008,861

[22] Filed: Jan. 20, 1998

[30] Foreign Application Priority Data

Jan. 17, 1997 [JP] Japan ................................. 9-017641

[51] Int. Cl.[7] ............................ A61B 6/00; H05G 1/02
[52] U.S. Cl. ........................ 378/196; 378/195; 378/208
[58] Field of Search .................................. 378/193, 195, 378/196, 197, 208, 209

[56] References Cited

U.S. PATENT DOCUMENTS

| | | | |
|---|---|---|---|
| 4,884,283 | 11/1989 | Koyama | 378/197 |
| 5,014,292 | 5/1991 | Siczek et al. | 378/196 |
| 5,038,371 | 8/1991 | Janssen et al. | 378/197 |
| 5,044,354 | 9/1991 | Goldhorn et al. | 378/196 |
| 5,199,060 | 3/1993 | Kato | 378/196 |
| 5,386,453 | 1/1995 | Harrawood et al. | 378/198 |
| 5,410,584 | 4/1995 | Schaefer et al. | 378/196 |
| 5,636,259 | 6/1997 | Khutoryansky et al. | 378/196 |
| 5,822,814 | 10/1998 | Van der Ende | 378/179 |

Primary Examiner—David P. Porta
Assistant Examiner—Drew A. Dunn
Attorney, Agent, or Firm—Antonelli, Terry, Stout & Kraus, LLP

[57] ABSTRACT

An X-ray radioscopic photographing apparatus comprises a top-board support frame for supporting a top board in the body axis direction of an examinee, a stand for supporting the top-board support frame so as to be rotatable about the body axis, a support for holding an X-ray tube unit and an X-ray image intensifier so as to be faced each other, a support member for holding the stand and supporting the support so as to be movable in the body axis direction, and a base portion for supporting the support member tiltably.

14 Claims, 6 Drawing Sheets

X-RAY RADIOSCOPIC APPARATUS

BACKGROUND OF THE INVENTION

The present invention relates to an X-ray radioscopic apparatus, and particularly to an art effectively applied to an X-ray radioscopic apparatus capable of X-ray diagnosing a wide range of an examinee from various directions.

PRIOR ART

First, the structure of a conventional apparatus is described below by referring to FIGS. 9 and 10.

Figure 9:
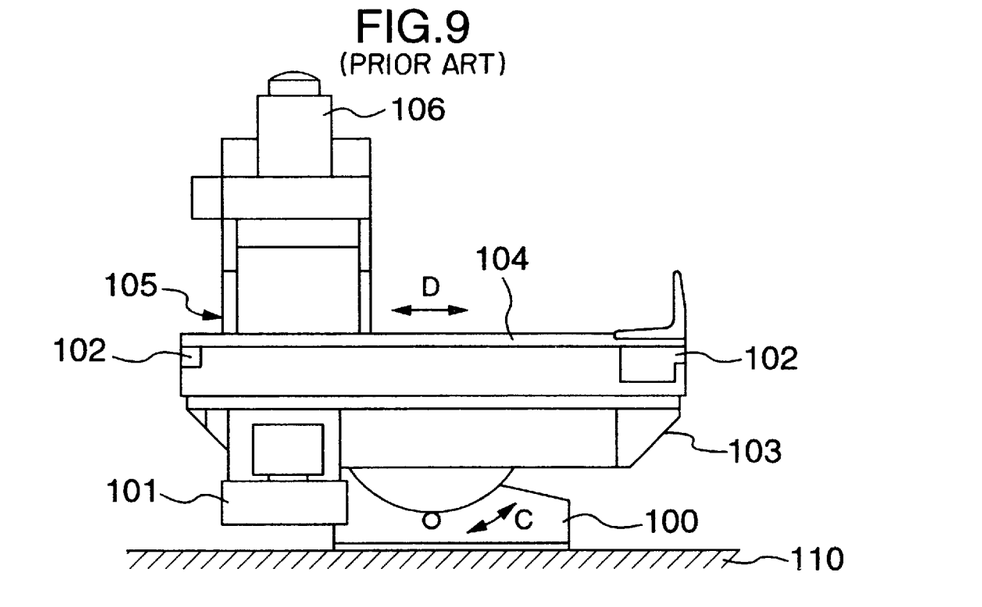
FIG. 9 is a front view showing a conventional top-board-sliding-type X-ray diagnostic table.
Figure 10:
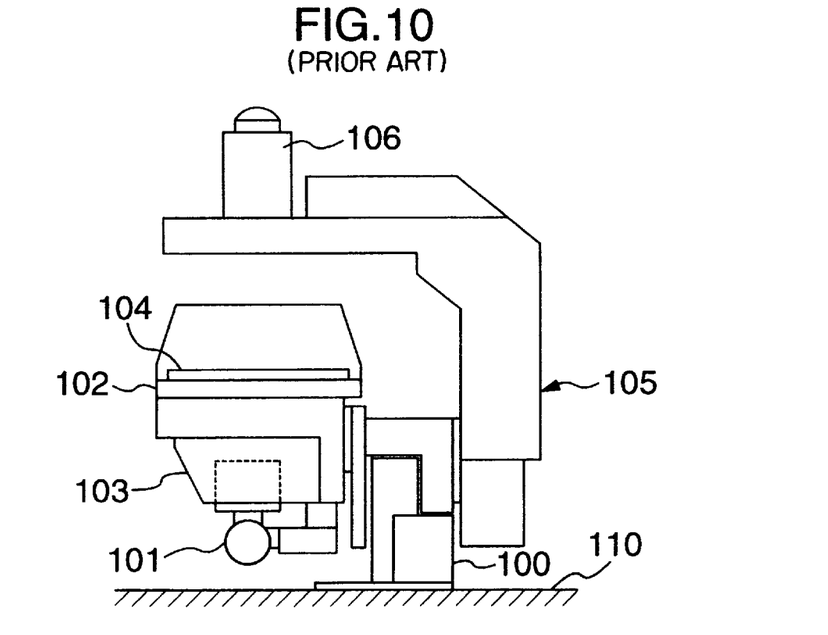
FIG. 10 is a top view of the table shown in FIG. 9.

A support frame 103 is so mounted on a base 100 secured to a floor surface 110 that the frame 103 can swing in the direction of the arrow C in FIG. 9. Support members are secured to opposite ends of the support frame 103 so as to support a top board 104. The top board 104 for mounting an examinee is so mounted on the upper sides of the support members 102 that the board 104 can slide in the direction of the arrow D in FIG. 9.

A support arm 105 is so supported by the support frame 103 that the arm 105 can slide between top-board support members 102 in the direction of the arrow D in FIG. 9. An X-ray tube unit 101 and an X-ray image intensifier (hereafter referred to as I.I.) 106 are provided at the both ends of the support arm 105 so as to face each other.

Not-illustrated electric driving portions are provided for a rotating portion of the support frame 103, a sliding portion of the top board 104, and a sliding portion of the support arm 105, respectively. These driving portions are actuated by an operator so as to position these members.

The swing motion of the support frame 103 in the direction of the arrow C in FIG. 9 enables to control the position of a contrast medium (e.g. barium) injected into the examinee on the top board 104 in the longitudinal direction of the examinee by means of gravity. Moreover, the sliding motions of the top board 104 and support arm 105 in the direction of the arrow D in FIG. 9 enable to X-ray diagnose the range from the head to lower limbs of the examinee without moving the examinee on the top board 104 by combining such motions of the board 104 and the arm 105.

Figure 11:
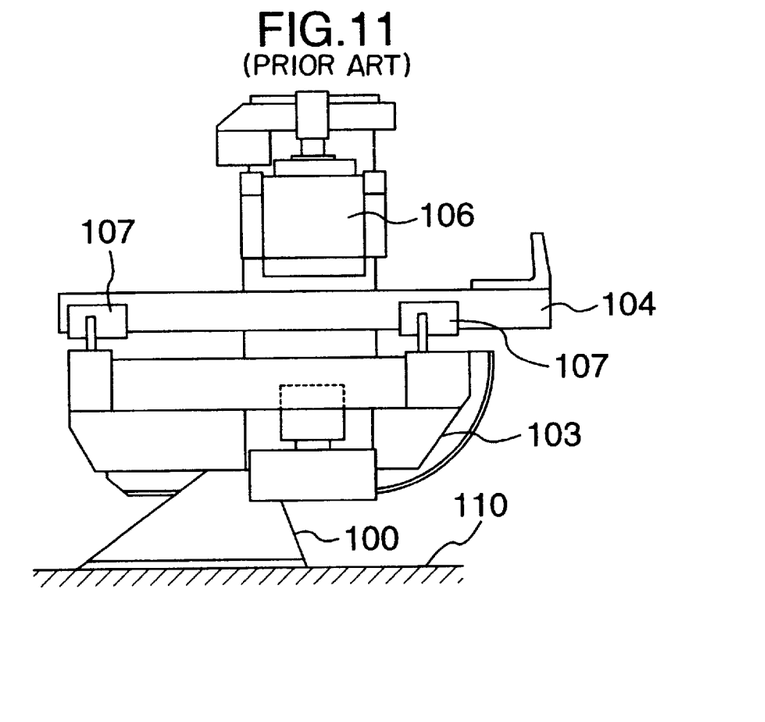
FIG. 11 is a front view showing a conventional top-board-rolling-type X-ray diagnostic table.
Figure 12:
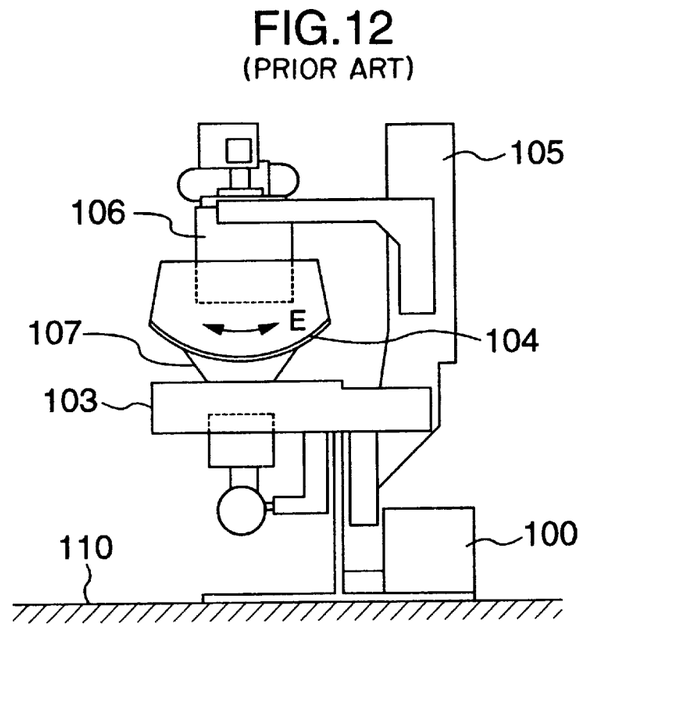
FIG. 12 is a side view of the table shown in FIG. 11.

Then, a conventional top-board-rolling-type x-ray diagnostic table is described below by referring to FIGS. 11 and 12.

The top-board-rolling-type X-ray diagnostic table has a structure almost same as that of the above-described top-board-sliding-type X-ray diagnostic table. The structures of the both types are different in the following points. In the case of the top-board-sliding-type X-ray diagnostic table, the top board 104 is supported so as to be slidable in its longitudinal direction. In the case of the top-board rolling type, however, top-board support members 107 are set nearby opposite ends of the support frame 103. Rolling mechanisms are provided in the members 107 for swinging the top board 104 in the direction of the arrow E in FIG. 12 about the rotational center on the exposed X-ray center line above the top board. The rolling mechanism comprises a roller guide provided in the top-board support member 107, a chain wound on the roller guide, and a motor for driving the roller guide and the chain. The swing motion or rolling motion of the top board 104 enables to control the position of a contrast medium injected into the examinee in the body width direction thereof the without moving the examinee on the top board.

SUMMARY OF THE INVENTION

However, the above-described conventional apparatuses have the following problems.

That is, in the case of the top-board-sliding-type X-ray diagnostic table, the top board 104 cannot swing (or roll). Therefore, when it is necessary to change the position of a contrast medium in the examinee in the body width direction thereof, the examinee must change his position in the direction. In the case of the top-board-rolling-type X-ray diagnostic table, the top board 104 cannot slide in the longitudinal direction of the examinee. Therefore, to perform X-ray inspection of a portion of the examinee such as lower limbs or head which cannot be X-ray-radioscopic-photographed only in the slidable range of the support arm 105 in the longitudinal direction of the top board, it is necessary to change the position of the examinee in the body length direction on the top board 104.

Therefore, even if the top-board sliding type or the top-board rolling type is used, it is impossible to inspect the entire body of the examinee in a wide range by optionally controlling the position of the contrast medium in the examinee in the body width direction thereof and thus, the inspection efficiency is lowered.

Moreover, it is considered to incorporate a conventional rolling mechanism into a conventional top-board-sliding-type X-ray diagnostic table so as to roll and slide the top board. In this case, however, a rolling mechanism is set on the sliding mechanism of the top board 104 in FIG. 9 and thus, the position of a top board from the floor surface is raised, the apparatus is complicated, and the operability is deteriorated.

An object of the present invention is to realize such two operations, i.e., top board sliding and top board rolling in a single X-ray diagnostic table while the position of a top board from the floor surface is the same as the case of a conventional apparatus.

An X-ray diagnostic apparatus of the present invention comprises a base portion provided on the floor surface upright, a support member supported by the base portion so as to swing in the vertical plane to freely change an angle of the support member relative to the floor surface, a support for supporting an X-ray tube unit and an X-ray image receptor at opposite ends thereof so as to face each other, and being supported movably along the support member, a top board for mounting an examinee, a top-board support frame for supporting the top board so as to move in a body axis direction of the examinee, and a stand for supporting the top-board support frame so as to swing about the body axis, the top board being supported to one end of the support member through the top-board support frame and the stand.

A center axis of the swing motion of the top-board support frame about the body axis of the examinee is present at a position above and nearby the surface of the top board on which the examinee is mounted and located at the center of the top board.

PREFERRED EMBODIMENTS OF THE INVENTION

An embodiment of the present invention is described below in detail with referring to the accompanying drawings.

Figure 1:
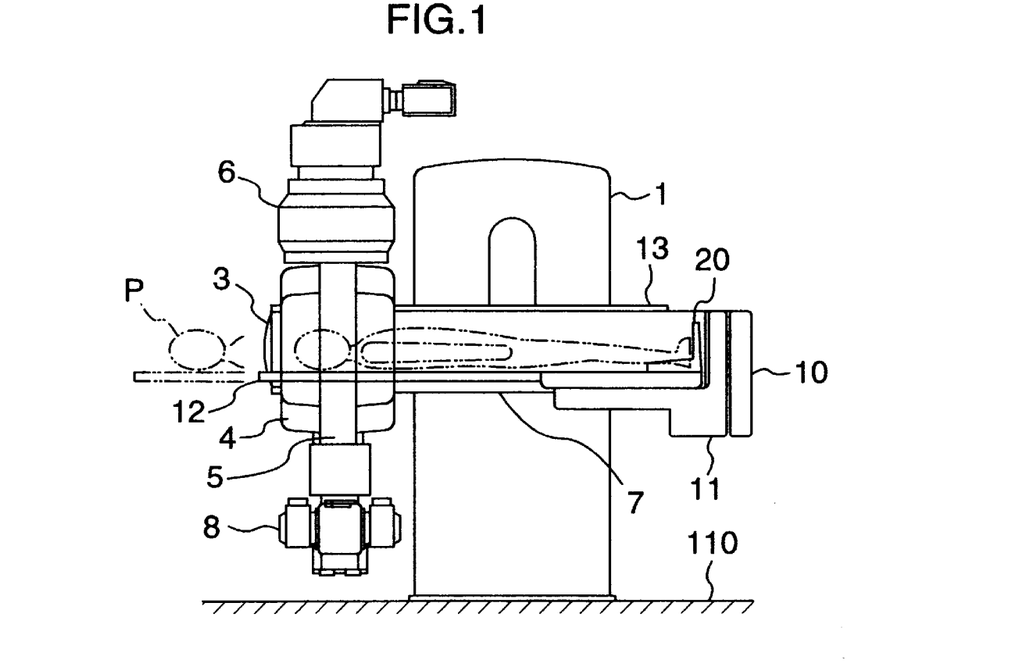
FIG. 1 is a front view of an X-ray radioscopic photographing apparatus of the present invention.
Figure 2:
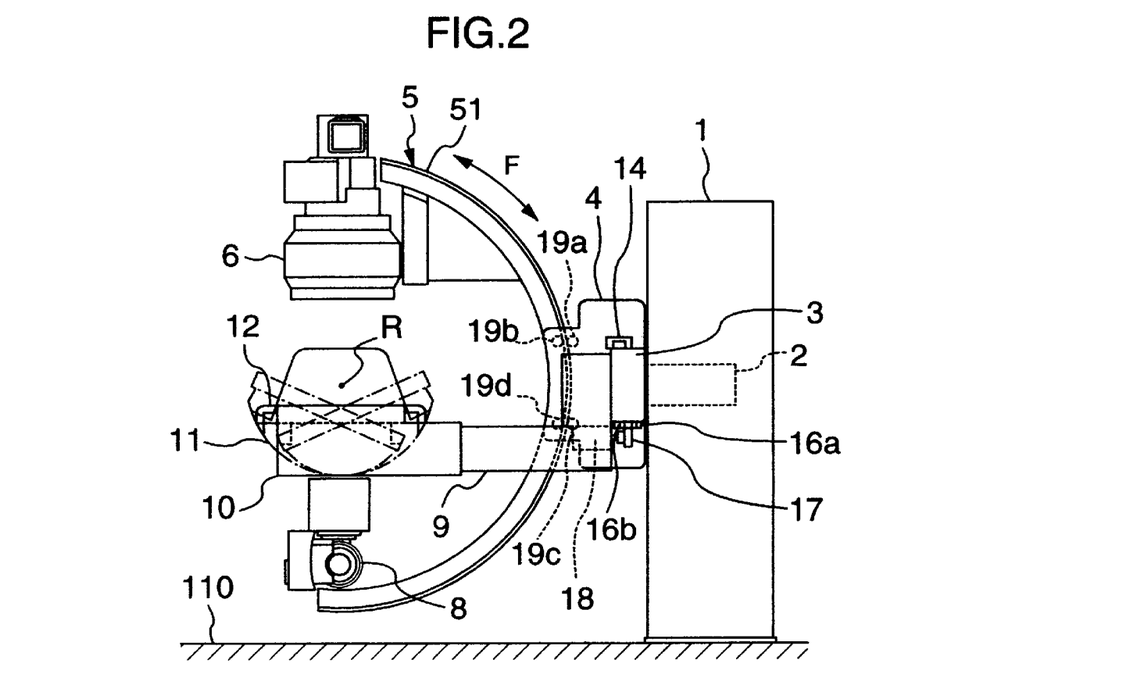
FIG. 2 is a right side view of the apparatus shown in FIG. 1.
Figure 3:
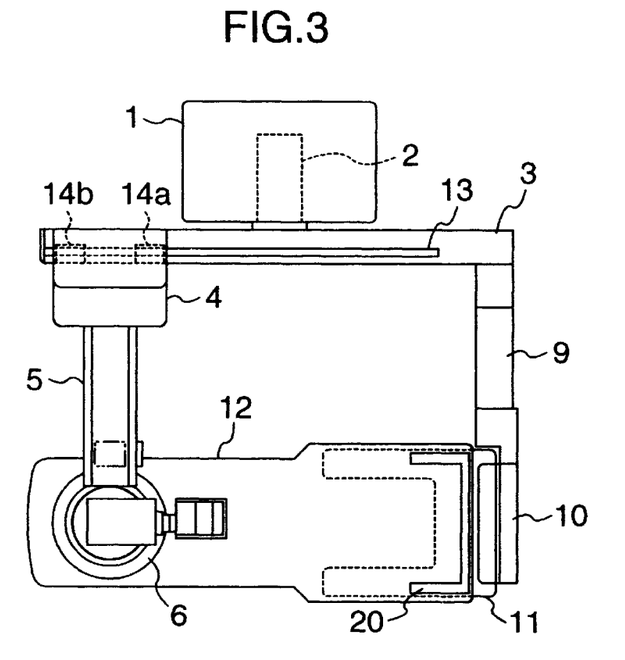
FIG. 3 is a top view of the apparatus shown in FIG. 1.

FIGS. 1 to 3 show a schematic structure of an X-ray radioscopic apparatus which is a mode (embodiment) of the present invention, and FIG. 1 is a front view of the apparatus, FIG. 2 is a side view of the apparatus shown in FIG. 1, and FIG. 3 is a top plan view of the apparatus shown in FIG. 1.

A shaft 2 secured to a support member 3 is supported by a base portion 1 secured to a floor surface 110 so as to be swingeable about an axis thereof. The shaft 2 is adapted to be swung by a not-illustrated conventional driving mechanism comprising, for example, a worm wheel, a worm gear, and a motor.

A holder 4 is mounted on the support member 3 so as to be linearly movable in the longitudinal direction of the support member 3. This mounting is realized by securing a linear guide bearing rail 13 and a rack 7 to the support member 3 and by securing two blocks 14a and 14b to be engaged with the rail 13 and guide rollers 16a and 16b for holding the both sides of the rack 7 in the holder 4.

Moreover, a motor 18 and a pinion 17 are set in the holder 4. Because the tooth flank of the pinion 17 engages with that of the rack 7, the holder 4 can be moved along the support member 3 by driving the motor 17.

An X-ray tube unit 8 and an image intensifier (hereinafter referred to as I.I.)6 are held at opposite ends of a C-shaped support 5 so as to be faced each other and constituted so that an examinee P can be X-ray-radioscopic-photographed by exposuring X-rays toward the examinee P from the X-ray tube unit 8 and converting X-rays passing through the examinee P into an optical image by the I.I. 6.

The support 5 has an arc shape, so that the examinee P can be radioscopic-photographed from various directions, which is supported by the holder 4 so as to be slidable in the direction of the arrow F in FIG. 2. This supporting is realized by securing guide rollers 19a, 19b, 19c, and 19d to the holder 4. The rollers 19a and 19b hold therebetween a protrusion 51 projected from an edge of one side of the support 5, and the rollers 19c and 19d hold therebetween a protrusion projected from an edge of opposite side of the support 5. Moreover, the support 5 is adapted to be slid by a not-illustrated conventional electrical driving mechanism such as a mechanism in which a chain is trained over the outer periphery of the support 5 and a chain wheel secured to the holder 4, and the chain wheel is rotated by a motor.

A stand holder 9 is secured to one end of the support member 3 and a stand 10 is secured to a tip end of the stand holder 9. A top-board support frame 11 is supported by the stand 10 so as to swing about a point R as shown in FIG. 2.

A top board 12 for mounting the examinee P is supported by the top-board support frame 11 so as to be slidable in the body axis direction of the examinee P. Furthermore, a footstool 20 is set to an end of the top board 12 in order to support the examinee P on the top board 12.

Then, supporting and driving mechanisms of the top board which are characteristic portions of the present invention are described below by referring to FIGS. 4 to 7. FIGS. 4 to 7 show a state of removing the footstool 20 from the top board 12 for convenience sake.

Figure 4:
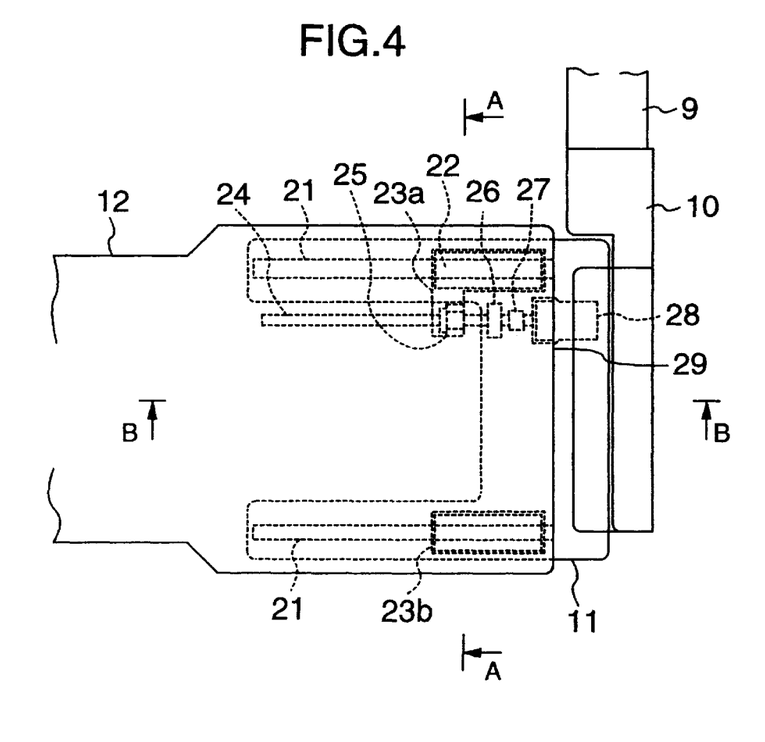
FIG. 4 is an enlarged top view of the rear end of the top board shown in FIG. 3.
Figure 5:
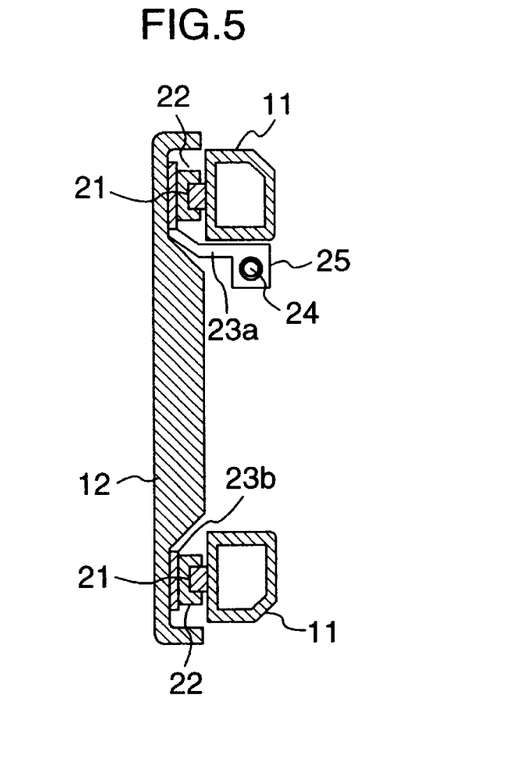
FIG. 5 is a sectional view taken along the line A—A in FIG. 4.

The top board 12 on which the examinee P is to be mounted includes a central portion having a high X-ray permeability, made of, for example, carbon-fiber, and edge portions located on opposite sides of the central portion, having no X-ray permeability. A fitting 23a and a mounting plate 23b are secured to underneath surfaces of the edge portions at the top board 12, respectively.

One block 22 of a linear guide bearing is secured to the mounting plate 23b. A nut 25 engaged with a driving screw 24 and another block 22 of the linear guide bearing are secured to the fitting 23a.

A rail 21 of the linear guide bearing is secured to an upper surface of each of both arms of the top-board support frame 11 so as to be in parallel. These rails 21, 21 are engaged with the blocks 22, 22. Furthermore, a bearing for supporting the driving screw 24 is secured to the top-board support frame 11. A one end of the driving screw 24 is connected through a coupling 27 to a shaft of a motor 28 secured to the top-board support frame 11 through a bracket 29. That is, the top board 12 is provided on the top-board support frame 11 by these supporting and driving mechanisms so as to be slidable in the body axis direction of the examinee.

Figure 6:
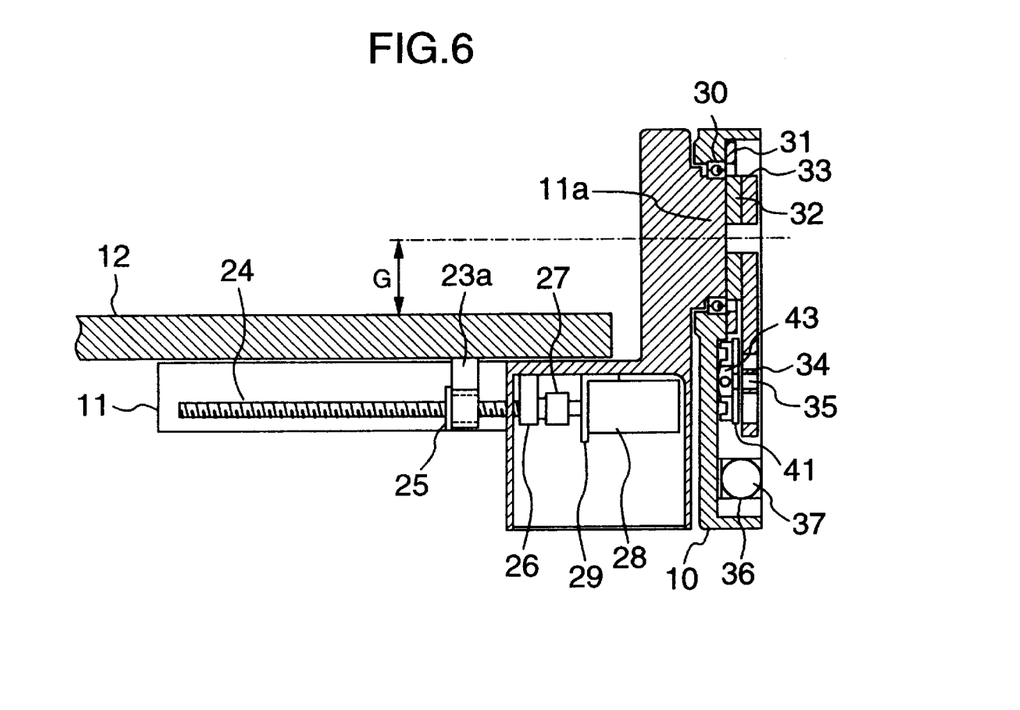
FIG. 6 is a sectional view taken along the line B—B in FIG. 4.

A shaft-shaped portion 11a is formed at the rear end of the top-board support frame 11, which is fitted to an inner race of a cross roller bearing 30, and a pressing piece 32 is secured to the shaft-shaped portion 11a to prevent the frame 11 from falling out from the bearing 30.

An outer race of the cross roller bearing 30 is secured to a recess formed on the stand 10 by a pressing plate 31. According this, the top-board support frame 11 is swingeably supported by the stand 10 so as to swing about a swing axis which extends through a center of the cross roller bearing 30.

The center of the cross roller bearing 30 corresponds to the point R in FIG. 2, and is located above and nearby the top board. A distance (dimension G in FIG. 6) between the surface of the top board 12 and the point R is about 10 cm. Accordingly the examinee mounted on the top board 12 is prevented from greatly deviating from the X-ray exposuring center even if the top board 12 is swung about the point R.

Figure 7:
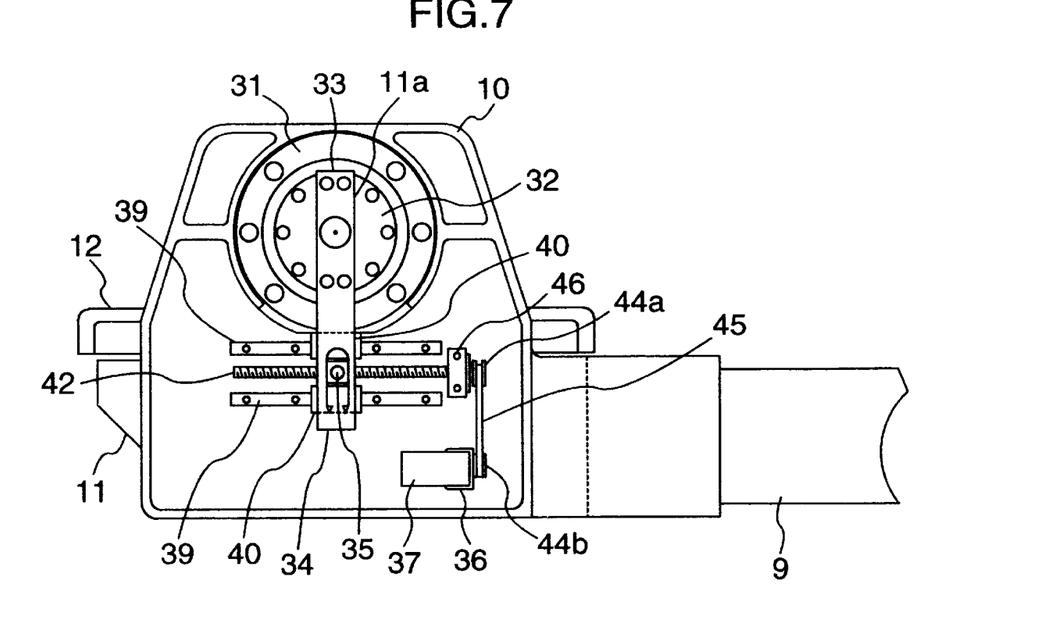
FIG. 7 is a right side view of the rear end of the top board shown in FIG. 4, showing a state of removing a cover from a stand.

Because a connecting rod 33 is at one end portion thereof secured to the pressing piece 32, the rod 33 swings in accordance with the swing motion of the top-board support frame 11. Moreover, an elongate slot is formed in the other end portion of the rod 33, and a rectangular block 34 is disposed in the slot so as to be slidable along the slot in the longitudinal direction of the rod 33. The block 34 is provided at a center thereof with a round hole into which a shaft portion 35 formed on a front surface of a slide plate 41 is inserted.

Two blocks 40, 40 of a linear guide bearing and a nut 43 engaged with a driving screw 42 are secured to a rear surface of the slide plate 41. The blocks 40 and 40 are engaged with rails 39 and 39 secured on the stand 10 in parallel.

The driving screw 42 is rotatably supported at one end portion thereof by a bearing 46 secured onto the stand 10 and a pulley 44a is set to the end of the driving screw 42. A belt 45 is applied between the pulley 44a and a pulley 44b attached to an output shaft of a motor 37 secured onto the stand 10 through a bracket 36, thereby transmitting the rotation of the output shaft of the motor 37 to the driving screw 42.

Figure 8:
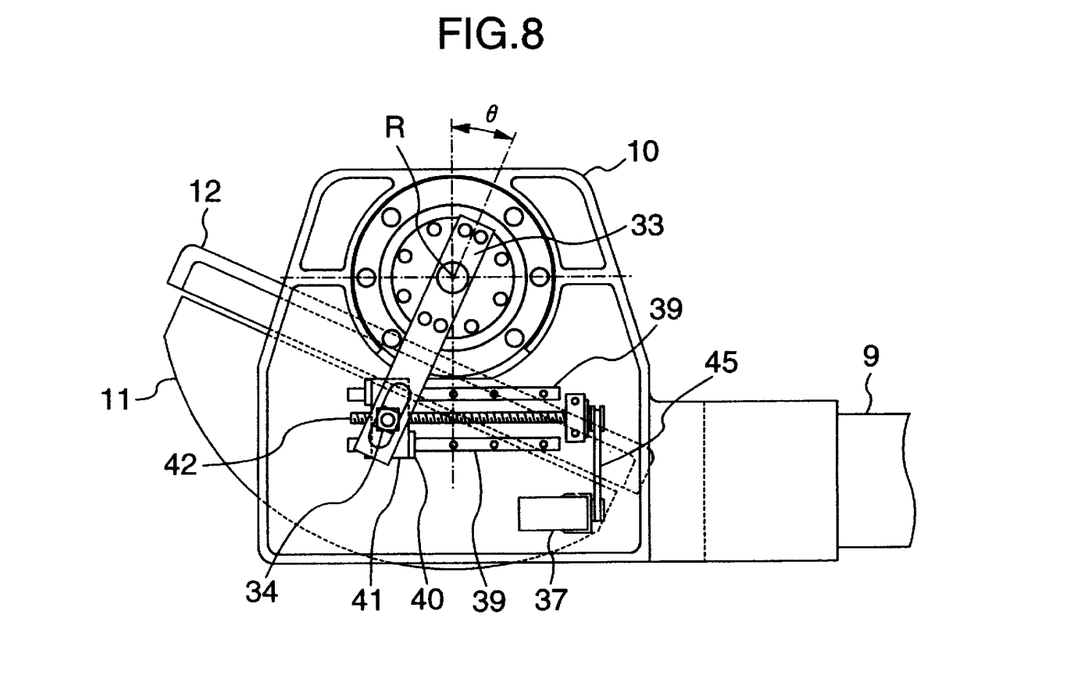
FIG. 8 is an illustration for explaining the operation of the top board.

The swinging and sliding motions of the top board 12 of the X-ray diagnostic apparatus of this embodiment are described hereinafter by referring to FIGS. 6 to 8. FIG. 8 shows the top board in a limit position in a swing motion thereof.

FIG. 6 shows the top board 12 in a limit position in a sliding motion thereof in the body axis direction of the examinee. When the motor 28 is driven, the rotation of the output shaft of the motor 28 is transmitted to the driving screw 24 through the coupling 27 and then the nut 25 is moved toward the head of the examinee by a distance corresponding to the rotation of the screw. Therefore, the top board 12 to which the nut 25 is secured slides on the top-board support frame 11.

FIG. 7 shows the top board 12 in a neutral position in a swing motion around the swing axis which extends through a center of the cross roller bearing 30. An operation of the swing motion of the top board 12 is as follows.

When the motor 37 is driven, the rotation of the output shaft of the motor 37 is transmitted to the driving screw 42 through the belt 45 and then the nut 43 is moved by a distance corresponding to the rotation of the screw 42. Therefore, the slide plate 41 to which the nut 43 is secured is linearly moved through the blocks 40 and 40 along the rails 39 and 39 of the linear guide bearing. Simultaneously, the block 34 moves together with the slide plate 41 while rotating around the shaft portion 35. Because one side of the block 34 contacts an inner surface of the slot formed in the rod 33, it is tilted by a tilt angle θ by means of the block 34. Therefore, the top-board support frame 11 for supporting the top board 12 swings about the swing axis which extends through the point R in clockwise direction by a tilt angle θ into a state shown in FIG. 8. As shown in FIGS. 2, 7 and 8, the swing axis which extends through the point R, is a central axis extending along the lengthwise direction of said table top-board 12. Further, the central axis is positioned centrally in a widthwise direction to said table top-board 12 and which is further located at a predetermined distance out of a plane of the surface of which the table top-board lies.

Accordingly, not only the sliding motion of the top board for mounting the examinee in the body axis direction (top board sliding motion) but also the swinging motion of the top board about the body axis (top board swinging motion) can be achieved in a single X-ray radioscopic apparatus.

In the case of this embodiment, the swing motion of the top board about the body axis is carried out by means of tilting the connecting rod. It may be possible that a belt or a chain is trained over the shaft-shaped portion 11a of the top-board support frame 11 and over a pulley or a sprocket attached to an output shaft of a motor, and is driven by the motor. Instead of the belt, a gear train may be used to rotate the shaft-shaped portion 11a of the frame 11.

Moreover, in the case of this embodiment, the top board 12 is cantilevered by the support member 3 through the support frame 11, the stand 10 and the stand holder 9. It may be possible to support the top board at opposite ends thereof by means of providing an arm for supporting the beneath of the top board in the other end of the support member in addition to the support frame 11.

According to the present invention, the top-board support frame is provided to support the top board slidably in the body axis direction of the examinee, the stand is provided at one end of the support member, which stand supports the top-board support frame swingably about the body axis of the examinee, the support for holding the X-ray tube unit and the I.I. is supported slidably in the body axis direction of the examinee along the support member, and the support member is swingably by the base portion for changing the examinee's posture from a horizontal position to a standing position. Therefore, a single X-ray fluoroscopic-radiographic apparatus enables a dual operation, a top board sliding operation and a top board rolling operation.

Therefore, it is possible to control the position of the contrast medium injected into the examinee mounted on the top board in not only the body axis direction but also the body width direction. Moreover, because the top board is slidable in the body axis direction, the examinee can be moved with respect to an X-ray applying area. Therefore, it is possible to X-ray diagnose the examinee in a wide range over the entire area of the examinee by combining the top board sliding and swinging motion with the body-axis-directional movement of the support member mounting the X-ray tube unit and the I.I. Therefore, it is possible to improve the X-ray diagnostic efficiency because it is unnecessary to change directions of the examinee or mounting positions of the examinee depending on an inspecting portion of the examinee on a top board.

What is claimed is:

1. An X-ray radiographic apparatus comprising:
   a base unit provided on a floor surface and extending upward with respect to the floor surface;
   a first support unit supported by said base unit so as to swing in a vertical plane to freely change an angle of said first support unit relative to the floor surface;
   a second support unit supported by said first support unit for supporting a table top-board proximate to one end thereof;
   a third support unit supported by said first support unit for supporting an X-ray tube unit and an X-ray image receptor at opposite ends thereof so as to face one another, and adapted to be movable in a lengthwise direction of said table top-board and to change a direction of X-ray irradiation for examination; and
   a driving unit for drivingly moving said table top-board on said second support unit independently of said second support unit in the lengthwise direction of said table top-board so as to enable examination of an entire length of an examinee lying on said table top-board.

2. An X-ray radiographic apparatus according to claim 1, wherein said driving unit enables movement of said table top-board on said second support unit without interference of said third support unit so as to enable examination of an entire length of an examinee lying on said table-top board.

3. An X-ray radiographic apparatus according to claim 1, further comprising a rolling unit for rolling said table top-board about a central axis alone the lengthwise direction of said table top-board, said central axis being positioned centrally in a widthwise direction of said table top-board and being located at a predetermined distance out of a plane of the surface of said table top-board.

4. An X-ray radiographic apparatus according to claim 1, wherein said driving unit includes a motor rotating a screw having a nut mounted thereon and secured to said table-top board.

5. An X-ray fluoroscopic-radiographic apparatus according to claim 3, wherein said rolling unit includes a motor driving a screw having a nut mounted thereon, the nut cooperating with a member extending through the axis located at the predetermined distance from said table-top board so as to enable rolling of said table-top board about the axis.

6. An X-ray radiographic apparatus comprising:
a base unit provided on a floor surface and extending upward with respect to the floor surface;
a first support unit supported by said base unit so as to swing in a vertical plane to freely change an angle of said first support unit relative to the floor surface;
a second support unit supported by said first support unit for supporting a table top-board proximate to one end thereof;
a third support unit supported by said first support unit for supporting an X-ray tube unit and an X-ray image receptor at opposite ends thereof so as to face one another, and adapted to be movable in a lengthwise direction of said table top-board and to change a direction of X-ray irradiation for examination; and
a rolling unit for rolling said table top-board about a central axis alone the lengthwise direction of said table top-board, said central axis being positioned centrally in a widthwise direction of said table top-board and being located at a predetermined distance out of a plane of the surface of said table top-board.

7. An X-ray fluoroscopic-radiographic apparatus according to claim 6, wherein said rolling unit includes a motor driving a screw having a nut mounted thereon, the nut cooperating with a member extending through the axis located at the predetermined distance from said table-top board so as to enable rolling of said table-top board about the axis.

8. An X-ray radiographic apparatus comprising:
a base unit provided on a floor surface and extending upward with respect to the floor surface;
a first support unit supported by said base unit so as to swing in a vertical plane to freely change an angle of said first support unit relative to the floor surface;
a second support unit supported by said first support unit for supporting a table top-board proximate to one end thereof;
a third support unit supported by said first support unit for supporting an X-ray tube unit and an X-ray image receptor at opposite ends thereof so as to face one another, and adapted to be movable in a lengthwise direction of said table top-board and to change a direction of X-ray irradiation for examination;
a rolling unit for rolling said table top-board about a central axis alone the lengthwise direction of said table top-board, said central axis being positioned centrally in a widthwise direction of said table top-board and being located at a predetermined distance out of a plane of the surface of said table top-board; and
a driving unit for drivingly moving said table top-board on said second support unit independently of said second support unit in the lengthwise direction of said table top-board so as to enable examination of an entire length of an examinee lying on said table top-board.

9. An X-ray fluoroscopic-radiographic apparatus according to claim 8, wherein said driving unit enables movement of said table top-board on said second support unit without interference of said third support unit so as to enable examination of an entire length of an examinee lying on said table-top board.

10. An X-ray fluoroscopic-radiographic apparatus according to claim 8, wherein said driving unit includes a motor rotating a screw having a nut mounted thereon and secured to said table-top board.

11. An X-ray radiographic apparatus comprising:
a base unit provided on a floor surface and extending upward with respect to the floor surface;
a first support unit supported by said base unit so as to swing in a vertical plane to freely change an angle of said first support unit relative to the floor surface;
a second support unit supported by said first support unit for supporting a table top-board proximate to one end thereof;
a third support unit supported by said first support unit for supporting an X-ray tube unit and an X-ray image receptor at opposite ends thereof so as to face one another, and adapted to be movable in a lengthwise direction of said table top-board and to change a direction of X-ray irradiation for examination;
a driving unit for drivingly moving said table top-board on said second support unit independently of said second support unit in the lengthwise direction of said table top-board; and
a rolling unit for rolling said table top-board about a central axis alone the lengthwise direction of said table top-board, said central axis being positioned centrally in a widthwise direction of said table top-board and being located at a predetermined distance out of a plane of the surface of said table top-board.

12. An X-ray radiographic apparatus according to claim 11, wherein said driving unit enables movement of said table top-board on said second support unit without interference of said third support unit so as to enable examination of an entire length of-an examinee lying on said table-top board.

13. An X-ray radiographic apparatus according to claim 11, wherein said driving unit includes a motor rotating a screw having a nut mounted thereon and secured to said table-top board.

14. An X-ray radiographic apparatus according to claim 11, wherein said rolling unit includes a motor driving a screw having a nut mounted thereon, the nut cooperating with a member extending through the axis located at the predetermined distance from said table-top board so as to enable rolling of said table-top board about the axis.

* * * * *